(12) United States Patent
Gong

(10) Patent No.: US 11,111,267 B2
(45) Date of Patent: Sep. 7, 2021

(54) CRYSTAL FORMS OF AN ANTITUMOR AGENT AND THEIR PREPARATION METHODS

(71) Applicant: Xianchang Gong, El Cajon, CA (US)

(72) Inventor: Xianchang Gong, El Cajon, CA (US)

(73) Assignee: Xianchang Gong, El Cajon, CA (US)

( * ) Notice: Subject to any disclaimer, the term of this patent is extended or adjusted under 35 U.S.C. 154(b) by 0 days.

(21) Appl. No.: 16/873,629

(22) Filed: May 26, 2020

(65) Prior Publication Data
US 2021/0047362 A1 Feb. 18, 2021

(51) Int. Cl.
C07J 69/00 (2006.01)
A61P 35/04 (2006.01)
A61P 35/00 (2006.01)

(52) U.S. Cl.
CPC ............... *C07J 69/00* (2013.01); *A61P 35/04* (2018.01); *C07B 2200/13* (2013.01)

(58) Field of Classification Search
CPC ............................. C07B 2200/13; C07J 69/00
See application file for complete search history.

(56) References Cited

PUBLICATIONS

Chen et al. (Helvetica Chemic Acta, 2013, 96(6), pp. 1072-1077).*

* cited by examiner

*Primary Examiner* — Susanna Moore

(57) ABSTRACT

The present invention provides two crystal forms of jervine and their preparation methods, and their application as antitumor agents. The preparation methods of these two crystal forms are simple, high yield and can be easily scaled to industry scale.

10 Claims, 5 Drawing Sheets

CRYSTAL FORMS OF AN ANTITUMOR AGENT AND THEIR PREPARATION METHODS

FIELD OF THE INVENTION

This invention relates to the crystal forms of an antitumor agent, specifically for the different crystal forms of jervine and their preparation methods and applications.

BACKGROUND

The hedgehog gene is a segment-polarity gene. It was identified in *Drosophila* and is named since the mutation of the embryo phenotype covered with pointy denticles resembles a hedgehog. Mammals have three Hedgehog homologues, Sonic Hedgehog (SHH), Indian Hedgehog (IHH) and Desert Hedgehog (DHH), to encode the Shh, Ihh and Dhh protein separately. Hh proteins are composed of two domains, an amino-terminal domain Hh-N, which has the biological signal activity, and a carboxy-terminal autocatalytic domain Hh-C, which cleaves Hh into two parts in an intramolecular reaction and adds a cholesterol moiety to Hh-N. Hh precursor protein in the endoplasmic reticulum by autocatalytic split into Hh-N and Hh-C into two parts, wherein Hh-C covalent binding cholesterol molecules, and transferred to a Hh-N of the carboxy terminal, followed by acyl transfer enzymes under the action of Hh-N aminoterminal cysteine occurs palmitoylated. Hh protein is only through the process of these post-translational modifications in order to get full functionality.

The Hedgehog signaling pathway which has long been known to control embryonic development is essential for numerous processes in cell proliferation and differentiation during and after embryogenesis. Hedgehog signaling pathway controls cell growth and proliferation, and tumor incidence is a uncontrolled cell growth and proliferation process. A large number of studies have shown that the abnormal activation of the Hedgehog signaling pathway lead to tumor occurrence. Many effector molecules (such as n-Myc, EGF, CyclinD, CyclinE, CyclinB, BMP, etc.) involved in tumor cell proliferation proved to be the target gene or downstream molecule of the hedgehog signaling pathway. Furthermore the Hedgehog signaling pathway has cross-cutting role in many other signaling pathways (such as Notch, Wnt, etc.) that regulate cell differentiation and proliferation. Therefore, the study of effect of Hedgehog signaling pathway on tumorigenesis and development is of great significance. In mammals, a variety of genes have been identified as a proto-oncogene or tumor suppressor gene Hedgehog signaling pathway; among these genes, Ptch1, Smo, Shh, Gli1 and Gli2 relate to the occurrence of skin cancer in particular basal cell carcinoma. Because the breast is an organ derived from the skin, so breast cancer may have an intrinsic link with skin cancer.

Hh signaling pathway plays a key role in normal development process, and its dysfunction may lead to a variety of human diseases and cancer, including basal cell cancer, brain cancer, lung cancer, prostate cancer, pancreatic cancer and other gastrointestinal cancer. Studies have shown that inhibition of this pathway can slow down the development of chidren's brain cancer and several kind of lung cancer. Therefore, the study of the Hh pathway is very important for the basic science and clinical studies. China has a high incidence of gastrointestinal cancer, stomach and esophageal cancer is the most common gastrointestinal cancer at our country. The mechanism study of Hh signaling pathway on gastrointestinal cancer, is of great significance for the prevention and treatment of cancer.

Basal cell carcinoma is one of the most common skin cancers. Even at a low mortality rate, basal cell carcinoma (BCC) still causes significant demage to patient's health. Radation, ultraviolet radiation, trauma and other conditions are all related to the incidence of basal cell carcinoma. Recent study proves that the Hedgehog signal pathway is essential in the pathogenesis of basal cell carcinoma.

Jervine is a naturally occurring chemical that belongs to the group of steroidal jerveratrum alkaloids. It is also named "jie li lu jian", "jie li lu an", "jie er wen" and "suan li lu jian" in Chinese. It is a teratogen isolated from the corn lily (*Veratrum californicum*) that causes usually fatal birth defects. In 1957 the US Department of Agriculture started an eleven-year investigation which led to the identification of cyclopamine and jervine as the cause of the birth defect. It does so by inhibiting the hedgehog signaling pathway (Hh), thereby inhibit the activity of the protein. Because mutations in the Hedgehog signaling pathway are associated with the pathogenesis of a variety of tumors, so jervine may become the treatment of tumors, especially basal cell carcinoma, medulloblastoma, lung cancer, pancreatic cancer, bile duct cancer, ovarian cancer, stomach cancer, brain cancer, esophageal cancer, liver cancer and other drugs. Jervine has a structure as:

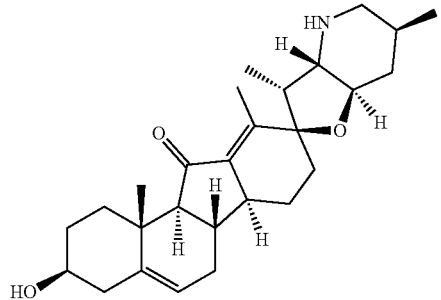

Li Lu (*Veratrum nigrum* L.) is a perennial herb. Its bulbs not enlargement obviously and has a chunky rhizome with many slender raw fleshy roots. Stems erect, full of dense white hairy stuff in the upper part while base of the plant always covered with brownish hairy fibers of vein from the rot sheath. Leaves grow alternate, ovaly shaped, lanceolate with narrowing base, clasping sheath-like petiole, green above and grayish green below. Panicles, stamens 6, anthers reniform, ovary with papillary hair. Column 3, growing from the top of the carpels. Capsul, winged seeds. Li Lu can be used as expectorant, emetic, insecticide. It can be used for the treatment of stroke phlegm, epilepsy, lymphangitis, malaria, mastitis, fractures, bruises, tinea capitis, scabies embolism, can also be used to kill maggots and flies. Li Lu is produced in northeast China, north China and Shanxi, Gansu, Shandong, Henan, Hubei, Sichuan and Guizhou. It grows at hillside forest or grass at about 1200-3000 meters altitude. There are different species of Li Lu include Guling Li Lu, Maohui Li Lu, Xingan Li Lu and Maoye Li Lu.

Different crystal forms of one compound have different bioavailabilities, so it is important to study the crystal forms for the formulation of orally available drugs.

THE INVENTION

The present invention provides crystal forms I and II of jervine, the crystal forms use X-ray powder diffraction with Cu-Ka radiation for characterization.

The present invention provides crystal form I, wherein the characteristic peaks represented by 2 θ angle (±0.2°) are positioned at 13.5097°、13.7117°、17.7732°、14.5810° in the X-ray powder diffraction pattern. Furthermore, the crystal form I of this invention, wherein the characteristic peaks represented by 2 θ angle (±0.2°) are positioned at 6.7399°、8.7103°、10.9690°、11.0651°、12.1224°、15.0048°、16.1113°、20.2443°、20.6768°、23.1278°、26.2035°、27.1966°、27.6453°、41.0536° in the X-ray powder diffraction pattern. Furthermore, the X-ray powder diffraction pattern of crystal form I is shown in picture 1.

The present invention provides crystal form II, wherein the characteristic peaks represented by 2 θ angle (±0.2°) are positioned at 13.6199°、13.3548°、14.6803°、15.0188°、14.4729°、20.7405°、20.9599°、17.1282°、8.8458°、16.3034° in the X-ray powder diffraction pattern.

Furthermore, the crystal form II of this invention, wherein the characteristic peaks represented by 2 θ angle (±0.2°) are positioned at 16.0515°、19.7802°、15.8398°、9.1034°、11.6825°、21.2135°、20.4846°、17.7607°、20.2196°、26.0347°、23.3938°、25.7750°、24.0115°、18.2995°、44.4657°、27.4530°、31.6225°、35.6230°、30.7323°、26.3009°、42.2070° in the X-ray powder diffraction pattern.

Furthermore, the X-ray powder diffraction pattern of crystal form II is shown in picture 2.

The present invention also provides methods to preprare the crystal form I and II of jervine.

A preparation method for the crystal form I of this invention, comprise the following steps:
1. Jervine is mixed with menthanol at room temperature for a clear solution,
2. remove menthanol till solid start to precipitate,
3. filter to obtain crystal form I.

A preparation method for the crystal form II of this invention, comprise the following steps:
(1) Jervine is mixed with acetonitrile at room temperature for a clear solution;
(2) remove acetonitrile till solid start to percipitate;
(3) filter to obtain crystal form II.

Jervine Preparation

The extraction method for jervine is by water or alcohol. The rhizomes of Li Lu was clearned and cutted to 1-2 cm pieces, followed by grounding into powders, to reflux for overnight using water or 95% eathanol as solvent. Jervine was obtained by chromatography using silica gel column after solvent was evaporated.

Pharmacological Tests of Jervine

1. The $IC_{50}$ of Jervine for Inhibition the Hedgehog Signaling Pathway

The $IC_{50}$ of jervine for inhibition the Hedgehog signaling pathway measured by reference method is 50 nM. This indicates jervine is a very strong hedgehog signaling pathway inhibitor.

2. Antitumor Effects of Jervine on Human Tumor Xenograft Models

Based on the fact that jervine can effectively inhibit the Hedgehog signal pathway, antitumor effects of jervine were evaluated using human tumor xenograft models inoculated subcutaneously. Tumor cell lines include pancreatic cancer cell line BXPC-3, lung cancer cell line NCI-H2122 and basal cell carcinoma cell line A431. The results (FIGS. 1-3) indicated while jervine can significantly inhibit the growth of these three tumors, no obvious side effects such as weight lose was observed. The results indicate jervine can significantly inhibit tumor growth, and is a good candidate for developing new antitumor drugs.

The following experiments were done too:

Pharmacokinetic Study of Jervine in Mice

The pharmacokinetic result of three CD-1 mice dosed jervine via oral gavage is shown in table 3. The bioavailability is 41%. PK result showed jervine can maintain certain concentration inside the animal's body which will help its antitumor effect.

Study the MTD of Jervine on BALB/c Nude Mice

BALB/c mice were dosed at 80 mg/kg via oral gauvage for 14 days; all mice were in good condition, no significant weight loss, no animal die. Result indicates the maximum tolerated dose of jervine is higher than 80 mg/kg for BALB/c mice.

Preparation of Hydrochloride Salt of Jervine

The hydrochloride acid salt of jervine was prepared by adding hydrochloride acid to a solution of jervine dissolved in anhydrous ethanol.

EXAMPLES

The following examples are used to describe the invention, but not to limit the invention.

Example 1: Preparation of Jervine 2 kg Li Lu from Sichuan province was grounded to powders, followed by extraction with 95% ethanol (2 L). The liquid was concentrated by vacuum to 350 g leftover. The leftover was dissolved in ethylacetate. Distilled water was used to wash the organic phase, the resulting aqueous phase was disregarded. The organic phase was dried by anhydrous sodium sulfate. The solvent in the organic phase was removed under vacuum, lead to 80 g concentrated raw material. The raw material was loaded on to a silica gel column and CHCl3-MeOH (20:1) was used for the chromatography. 200 mg jervine was obtained at the end.

Example 2: Preparation of Crystal Form I

Figure 1:
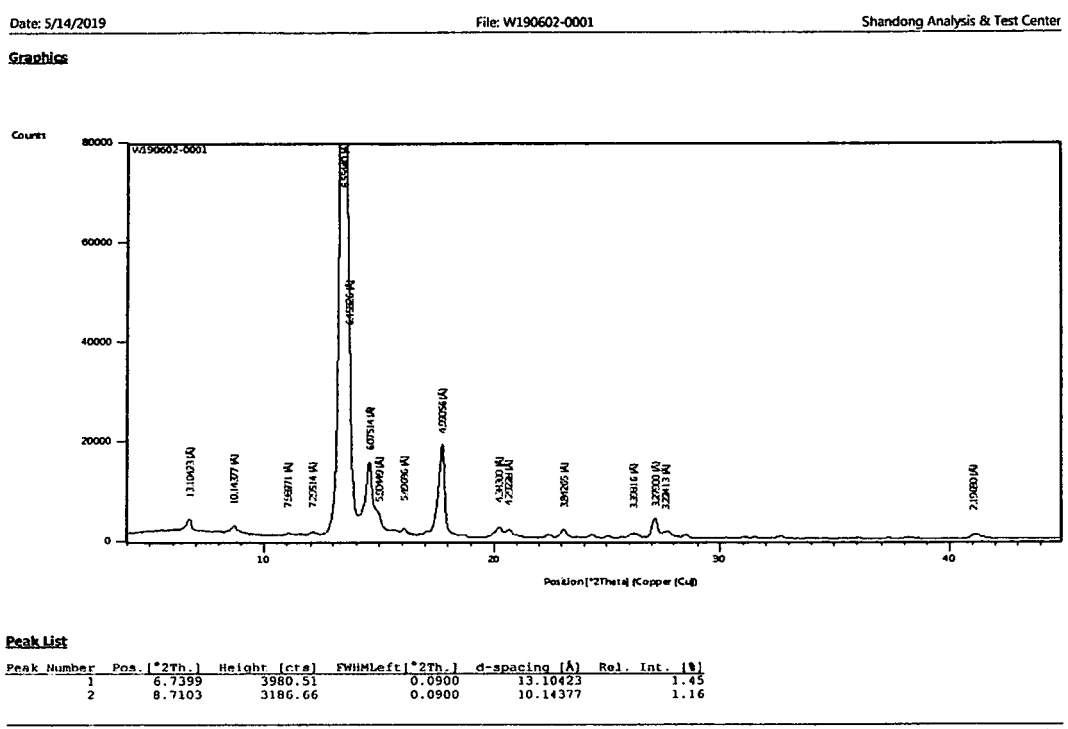
FIG. 1 X-ray powder diffraction pattern of crystal form I
FIG. 2 X-ray powder diffraction pattern of crystal form II
FIG. 3 The antitumor effect of jervine and GDC-0449 on the NCI-H2122 lung cancer model in BALB/c nude mice
FIG. 4 The antitumor effect of jervine and GDC-0449 on the A431 basal cell carcinoma model in BALB/c nude mice
FIG. 5 The antitumor effect of jervine and GDC-0449 on the BXPC-3 pancreatic cancer model in BALB/c nude mice

Jervine (300 mg) was dissolved in methanol (300 ml), solvent was removed using rotary evaporator till solid start to pericipitate, cooling in refrigerator, filter to obtaining crystal form I, its XRPD spectrum is shown in FIG. 1.

Example 3: Preparation of Crystal Form II

Figure 2:
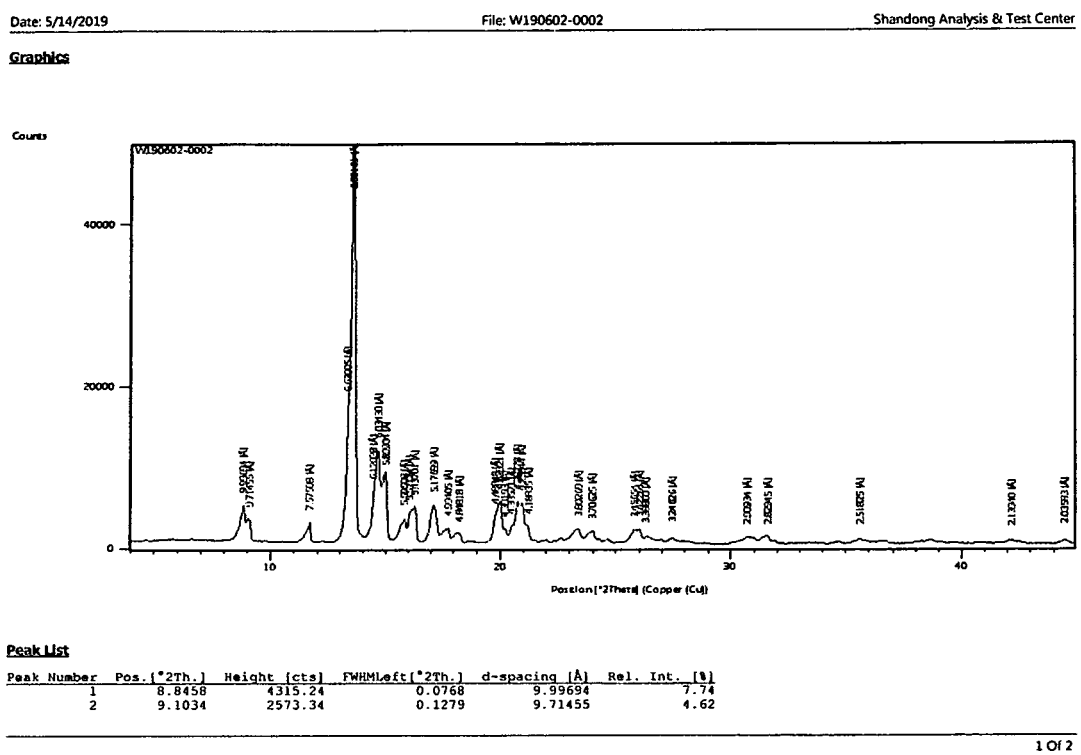

Jervine (300 mg) was dissolved in acetonitrile (300 ml), solvent was removed using rotary evaporator till solid start to pericipitate, cooling in refrigerator, filter to obtaining crystal form II, its XRPD spectrum is shown in FIG. 2.

Example 4: In Vitro Test: Experimental Method to Measure the Inhibition of Jervine on the Hedgehog Signaling Pathway 4.1 Cell Culture Hedgehog signaling pathway Gli Reporter-NIH3T3 cells were cultured in DMEM medium with 10% Calf serum, 1% Penn-strep, 500 μg/ml of Geneticin.

4.2 Measurement Method

To perform the Gli luciferase reporter assay, Gli Reporter—NIH3T3 cells were seeded at 25,000 cells per well into white clear-bottom 96-well microplate in 100 μl of growth medium. Cells were incubated at 37° C. and 5% CO2 for overnight. Next day remove the medium from wells and add 45 μl of diluted inhibitor in assay medium (Opti-MEM Reduced Serum Medium+0.5% calf serum+1% non-essential amino acids+1 mM Na-pyruvate+10 mM HEPES+1% Pen/Strep) per well. Incubate cells at 37° C. in a $CO_2$ incubator for 2 hours. Then add 5 μl of diluted mShh in assay medium to wells (final [mShh]=1 μg/ml). Add 55 μl of assay medium to cell-free control wells. Cells were treated for 27 hours. After treatment, cells were lysed and luciferase assay was performed using ONE-Glo luciferase assay system: add 50 μl of One-Glo Luciferase reagent per well and rock at room temperature for ~20 minutes. Luminescence was measured using a luminometer (BioTek Synergy™ 2 microplate reader)

4.3 Data Analysis

Reporter assays in triplicate were performed at each concentration. The luminescence intensity data were analyzed using the computer software, Graphpad Prism. In the absence of the compound, the luminescence intensity ($L_t$) in each data set was defined as 100%. In the absence of cells, the luminescence intensity ($L_b$) in each data set was defined as 0%. The percent luminescence in the presence of each compound was calculated according to the following equation: % Luminescence=$(L-L_b)/(L_t-L_b)$, where L=the luminescence intensity in the presence of the compound, $L_b$=the luminescence intensity in the absence of cells, and $L_t$=the luminescence intensity in the absence of the compound.

The values of % luminescence versus a series of compound concentrations were then plotted using non-linear regression analysis of Sigmoidal dose-response curve generated with the equation $Y=B+(T-B)/1+10^{((Log\ EC50-X) \times Hill\ Slope)}$, where Y=percent luminescence, B=minimum percent luminescence, T=maximum percent luminescence, X=logarithm of compound and Hill Slope=slope factor or Hill coefficient. The IC50 value was determined by the concentration causing a half-maximal percent activity.

The IC50 of jervine inhibiting the Hedgehog signal pathway is 50 nM measured by the above experiment.

Example 5: The Antitumor Effect and Toxicity Study of Jervine on NCI-H2122 and A431 Xenograft Tumor Model Using BALB/c Nude Mice Inoculated Subcutaneously The antitumor effect and toxicity study of jervine and GDC-0449 on NCI-H2122 and A431 xenograft tumor model were studied using BALB/c nude mice inoculated subcutaneously.

1. Cell Culture

NCI-H2122 cells were cultured in RMPI1640 medium, A431 tumor cells cultured in DMEM medium, all the medium were supplemented with 10% heat inactivated fetal bovine serum, all cells used EDTA containing trypsin, passaged twice a week, incubated at 37° C. in an atmosphere of 5% CO2 in air and cultured.

2. Experimental Animals

110 BALB/c nude mice, female, 6-8 weeks old, 18-22 g in body weight, were purchased from Shanghai Laboratory Animal Center (SLAC, Shanghai, China). The mice were kept in individually ventilated cage (IVC) systems at constant temperature and humidity, with 20.5-24.5° C. for temperature, 40-75% for humidity. With 4 animals in each cage, the size ogf the cage is 325 mm×210 mm×180 mm. The bedding material is corn cob, which is changed twice per week. Animals had free access to irradiation sterilized dry granule food and water during the entire study period. The food and water were changed twice per week. The identification labels for each cage contain the following information: number of animals, sex, strain, and date received treatment, study number, group number, and the starting date of the treatment. Animals were marked by ear coding. The experiments started one week after receiving the animals.

3. Cell Inoculation

Each mouse were inoculated subcutaneously at the right flank region with NCI-H2122 tumor cells ($5 \times 10^7$/ml), NCI-H1703 tumor cells ($1 \times 10^8$/ml) and A431 tumor cells ($5 \times 10^7$/ml), respectively in a mixture of phosphate-buffered saline and matrigel for tumor development via a 1 ml syringe. The treatments were started when the mean tumor size reached about 200 (150-250) $mm^3$. The test articles administration and the animal numbers in each study group were shown in table 1.

TABLE 1

| Group | N | Treatment | Dose (mg/kg) | Dosing Route | Schedule |
|---|---|---|---|---|---|
| 1 | 8 | Vehicle Control | 0 | p.o. | QD × 21 days |
| 2 | 8 | Jervine | 40 | p.o. | QD × 21 days |
| 3 | 8 | Jervine | 60 | p.o. | QD × 21 days |
| 4 | 8 | Jervine | 80 | p.o. | QD × 21 days |
| 5 | 8 | GDC-0449 | 40 | p.o. | QD × 21 days |

Note:
N: animal number;
p.o. oral administration,
QD: once every day,
Administration volume: 0.1 ml/10 g,
Administration time will be adjusted after 15% weights lose.

4. Randomized Grouping

To avoid errors between groups, the animals were first grouped by the tumor volumes according to the tumor volume measurements, and then randomly re-assigned to different groups.

5. Observations

During the study, the care and use of animals were conducted in accordance with the regulations of the Association for Assessment and Accreditation of Laboratory Animal Care (AAALAC). After tumor cell inoculation, the animals were checked daily for morbidity and mortality. At the time of routine monitoring, the animals were checked for any effects of tumor growth and treatments on normal behavior such as mobility, visual estimation of food and water consumption, body weight gain/loss, eye/hair matting and any other abnormal effect.

6. Aseptic

The preparation of the solutions of the test articles, observation, dosing, measurement of the tumor and the body weight were all done in a biological safety cabinet.

7. Data Processing

After tumor volume reached 3000 mm³ or average tumor volume reached 2000 mm³, before experimental animals emaciated or coma, anesthesia and euthanasia will be performed. During the experiment, if the weight loss of experimental animal reaches 20%, administration will be discontinued and experimental animals will be observed until the weight returned to 10% range before restart of the administration. In this experiment, when the mean tumor volume reached 2000 mm³ or at the end of 59 days after the administration, experimental animals will be anesthesiaed to collect tumor mass which will be weighed and photographed.

8. Measurement 8.1 Tumor size was measured twice weekly in two dimensions using a caliper, and the volume was expressed in mm³ using the formula: $V=0.5 \, a \times b^2$ where a and b are the long and short diameters of the tumor, respectively.

8.2 T/C, percent value, T and C were the mean volume of the treated and control groups, respectively, on a given day.

8.3 T−C, calculated with T as the time (in days) required for the mean tumor size of the treatment group to reach a predetermined size, and C was the time (in days) for the mean tumor size of the control group to reach the same size.

8.4 $(1-((Td-T0)/(Cd-C0))) \times 100\%$ value (in percent) was an indication of antitumor effectiveness, Td and Cd were the mean tumor volumes of the treated and vehicle control animals on a given day and T0 and C0 were the mean tumor volumes of the treated and vehicle control animals at the start of the experiment.

8.5 Tumor mass weight was measured at the end of study.

9. Statistical Analysis

A one-way analysis of variance was performed followed by multiple comparison procedures. All data was analyzed using SPSS 18.0. $*p<0.05$ or $**P<0.01$ are generally considered statistically significant when compared with vehicle group.

Results showed jervine can effectively inhibit the tumor growth in a NCI-2122 human cancer xenograft model, the T/C value at dose levels of 40 mg/kg, 60 mg/kg and 80 mg/kg for 21 days is 0.79, 0.701 and 0.594. The T/C value for the test compound GDC-0449 is 0.794 at a dose level of 40 mg/kg. The experimental result was shown in FIG. 1. There was no significant of weight lose of the mice during the experiment.

Results showed jervine can effectively inhibit the tumor growth in A-431 xenograft tumor model, the T/C value at dose levels of 40 mg/kg, 60 mg/kg and 80 mg/kg for 21 days is 0.52, 0.80 and 0.82. The T/C value for the test compound GDC-0449 is 0.89 at a dose level of 40 mg/kg. The result was shown in FIG. 2. The experimental result was shown in FIG. 2. There were no significant of weight lose of the mice during the experiment.

Example 6: The Antitumor Effect and Toxicity Study of Jervine on BXPC-3 Xenograft Tumor Model Using BALB/c Nude Mice Inoculated Subcutaneously The antitumor effect and toxicity study of jervine and GDC-0449 on BXPC-3 xenograft tumor model were studied using BALB/c nude mice inoculated subcutaneously.

Cell Culture

BXPC-3 tumor cells cultured in RMPI1640 medium supplemented with 10% heat inactivated fetal bovine serum, all cells used EDTA containing trypsin, passaged twice a week, incubated at 37° C. in an atmosphere of 5% CO2 in air and cultured.

Experimental Animal

BALB/c nude mice, female, 6-8 weeks old, 18-22 g in body weight, were purchased from Shanghai Laboratory Animal Center (SLAC, Shanghai, China).

Cell Inoculation

Each mouse was inoculated subcutaneously at the right flank region with BXPC-3 tumor cells ($5 \times 10^7$) in 0.1 ml of phosphate-buffered saline with matrigel via a 1 ml syringe for tumor development. The treatments were started when the mean tumor size reaches approximately 200 (150-250) mm³ at 9 days after inoculation. The test article administration and the animal numbers in each study group are shown in table 2.

TABLE 2

| Group | N | Treatment | Dose (mg/kg) | Dosing Route | Schedule |
| --- | --- | --- | --- | --- | --- |
| 1 | 8 | Vehicle Control | 0 | iv | QD × 21 days |
| 2 | 8 | Jervine | 20 | iv | QD × 21 days |
| 3 | 8 | Jervine | 40 | iv. | QD × 21 days |
| 4 | 8 | Jervine | 80 | iv | QD × 21 days |
| 5 | 8 | GDC-0449 | 40 | iv | QD × 21 days |

Note:

N: animal number;

p.o. oral administration,

QD: once every day,

Administration volume: 0.1 ml/10 g,

Administration time will be adjusted after 15% weights lose.

Randomized grouping, observations, aseptic, data processing, measurement and statistical analysis are as described in Example 3.

Figure 3:
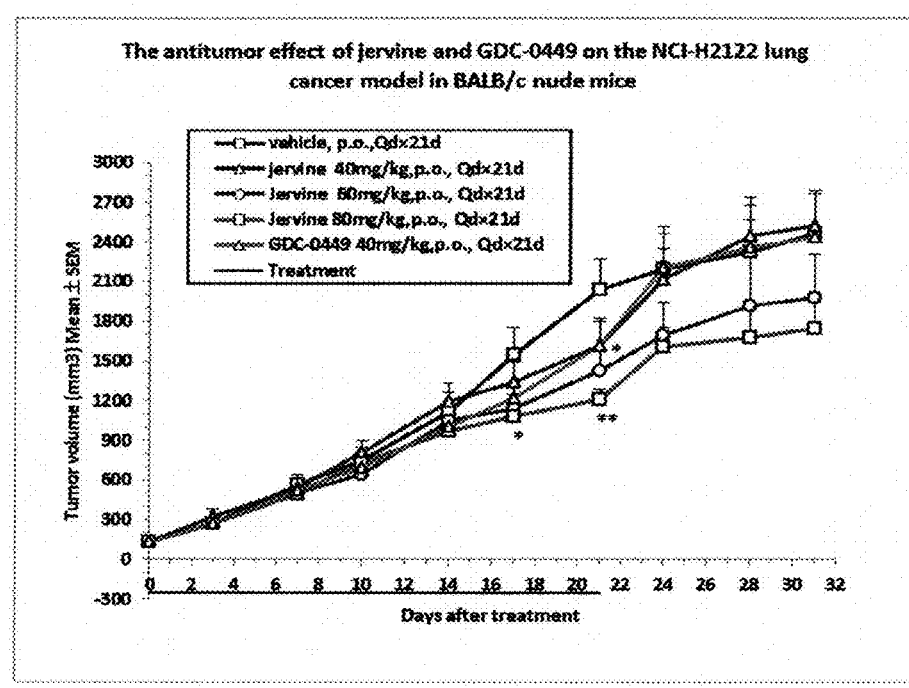
Figure 4:
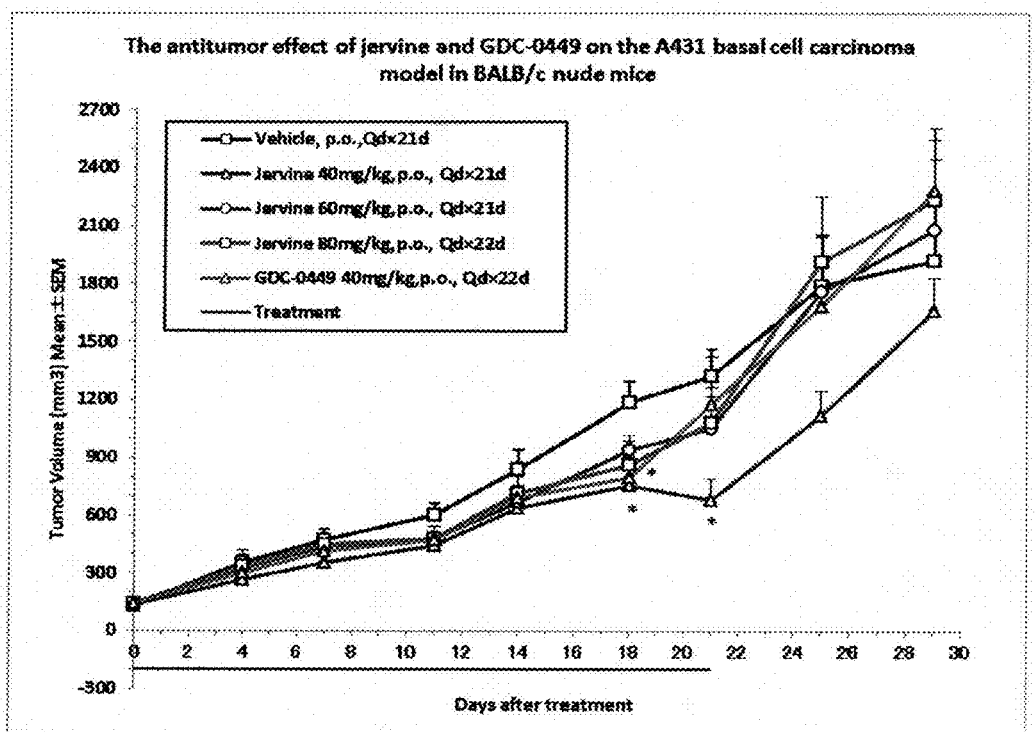
Figure 5:
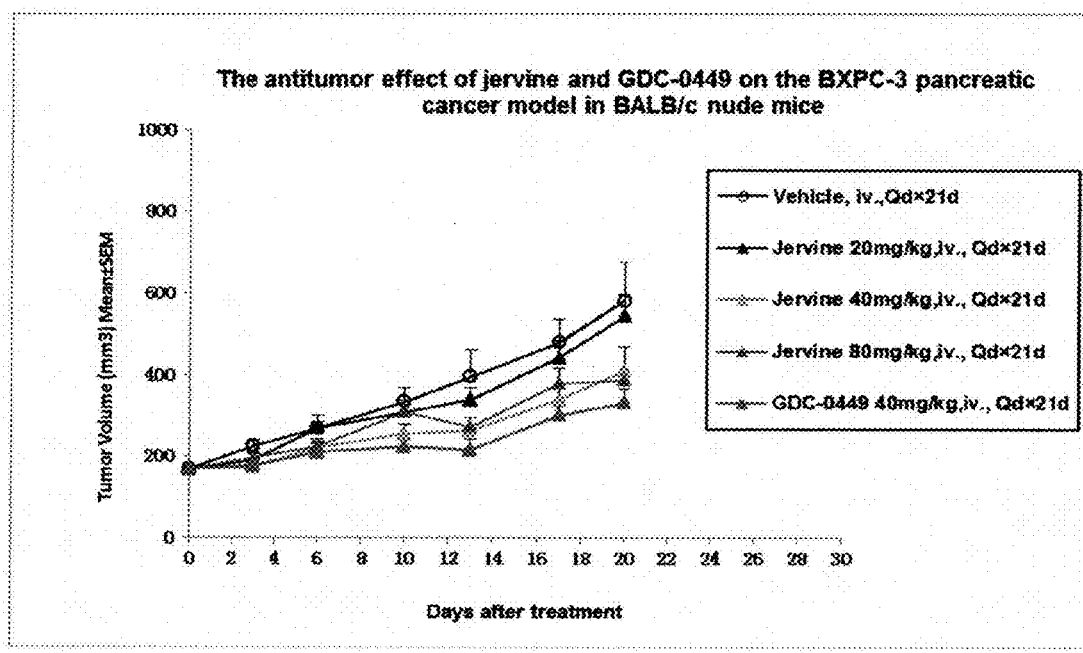

Results showed jervine can effectively inhibit the tumor growth in a BXPC-3 human pancreatic carcinoma xenograft model, the T/C value at dose levels of 20 mg/kg, 40 mg/kg and 80 mg/kg is 25.8%, 59.1% and 54.2%. The T/C value for the test compound GDC-0449 is 80.7% at a dose level of 40 mg/kg. Result was shown in FIG. 3. There were no significant of weight lose of the mice during administration.

Example 7: Pharmacokinetic Study of Jervine

Orally dosed: A total of 3 male experimental CD-1 mice, approximately 8 weeks of age at receipt was administered jervine via oral gavage at 10 mg/kg. Blood samples (300 µL) were collected via cardiac puncture predose and at 2 minute, 5 minute, 15 minute, 0.5 hour, 1 hour, 2 hour, 4 hour, 8 hour, 24 hours postdose. Plasma was made form the blood samples in order to measure the concentration of jervine. The PK data is shown in table 3, average bioavailability is 41.2%. The experimental data suggests jervine can maintain a certain concentration inside the body, which will help its antitumor effect.

TABLE 3

| | | | pharmacokinetic result of jervine in mice | | | | |
|---|---|---|---|---|---|---|---|
| PK Parameters | Cmax ng/mL | T1/2 hr | CL L/hr | Vz L | AUC(0-t) ng*hr/mL | AUC(0-inf) ng*hr/mL | F % |
| PO 10 mg/Kg | 368 | 11.8 | 0.13 | 0.68 | 1794 | 2260 | 41.2 |

Example 8: Study the MTD of Jervine on BALB/c Nude Mice

9 BALB/c nude mice were divided equally into 3 groups. The mice were orally dosed at 50 mg/kg, 80 mg/kg and 150 mg/kg by groups. Two mice in the 150 mg/kg treatment group were dead, there was no animal dead in the other two groups after 14 days treatment. It was initially determined that the MTD is higher than 80 mg/kg for BALB/c nude mice.

Example 9: Preparation of Jervine Hydrochloride Acid Salt

Jervine (1 g) was dissolved in anhydrous ethanol (30 ml) by heating. After the solution cooled to room temperature, hydrochloride acid was added drop by drop till white precipitate was formed. Jervine hydrochloride acid salt (1 g) was obtained after filtration and heat drying.

The invention claimed is:

1. A crystalline form of the compound Jervine of Formula 1, wherein the crystalline form is Form I, and has an X-ray powder diffraction (XRPD) pattern comprising peaks at diffraction angle 2θ(±0.20) degrees of 13.5097°, 13.7117°, 17.7732° and 14.5810° when irradiated with a Cu-Kα light source:

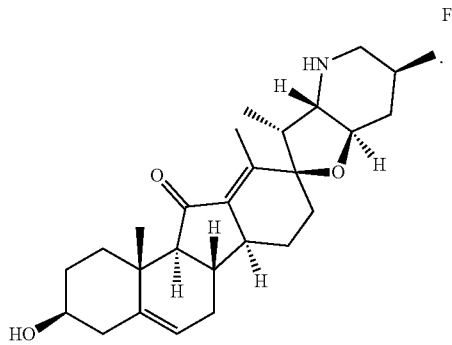

Formula I

2. The crystalline form I of claim 1, wherein the crystalline form further comprises peaks at diffraction angle 2θ(±0.20) degrees of 6.7399°, 8.7103°, 10.9690°, 11.0651°, 12.1224°, 15.0048°, 16.1113°, 20.2443°, 20.6768°, 23.1278°, 26.2035°, 27.1966°, 27.6453° and 41.0536° when irradiated with a Cu-Kα light source.

3. The crystalline form I of claim 1, wherein the crystalline form I has an X-ray powder diffraction spectrum pattern of FIG. 1.

4. A preparation method for the crystalline form I of claim 1, comprising the following steps: (1) mixing Jervine with methanol at room temperature until a clear solution is formed; and (2) removing the methanol until solid starts to precipitate, followed by filtering to obtain the crystalline form I of Jervine.

5. A pharmaceutical agent, wherein the agent contains a therapeutically effective amount of the crystalline form I of claim 1 and a pharmaceutically acceptable carrier and/or an excipient.

6. A crystalline form of the compound Jervine of Formula 1, wherein the crystalline form is Form II, and has an X-ray powder diffraction (XRPD) pattern comprising peaks at diffraction angle 2θ(±0.20) degrees of 8.8458°, 13.3548°, 13.6199°, 14.4729°, 14.6803°, 15.0188°, 16.3034°, 17.1282°, 20.7405° and 20.9599° when irradiated with a Cu-Kα light source:

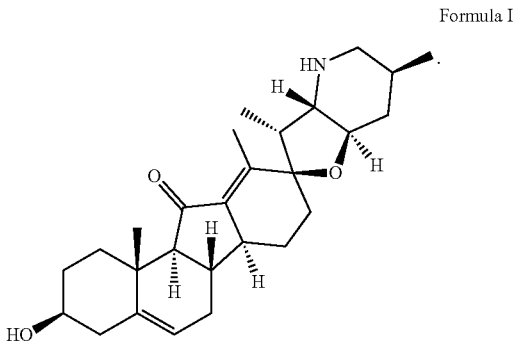

Formula I

7. The crystalline form II of claim 6, wherein the crystalline form further comprises peaks at diffraction angle 2θ(±0.20) degrees of 9.1034°, 11.6825°, 15.8398°, 16.05150°, 17.7607°, 18.2995°, 19.7802°, 20.2196°, 20.4846°, 21.2135°, 23.3938°, 24.0115°, 25.7750°, 26.0347°, 26.3009°, 27.4530°, 30.7323°, 31.6225°, 35.6230°, 44.4657° and 42.2070° in the X-ray powder diffraction pattern.

8. The crystalline form II of claim 6, wherein the crystalline form II has an X-ray powder diffraction spectrum pattern of FIG. 2.

9. A preparation method for the crystalline form II of claim 6, comprising the following steps: (1) mixing Jervine with acetonitrile at room temperature until a clear solution is formed; and (2) removing the acetonitrile until solid starts to precipitate, followed by filtering to obtain the crystalline form II of Jervine.

10. A pharmaceutical agent, wherein the agent contains a therapeutically effective amount of crystalline form II of claim 6 and a pharmaceutically acceptable carrier and/or an excipient.

* * * * *